(12) United States Patent    (10) Patent No.:    US 12,642,593 B2

Anso Romeo et al.    (45) Date of Patent:    Jun. 2, 2026

(54) INTERVENTION DEVICE WITH ELECTRODES

(71) Applicants: Universitat Bern, Bern (CH); EMPA Eidgenossische Forschungsanstalt, Duberdorf (CH)

(72) Inventors: Juan Anso Romeo, Bern (CH); Stefan Weber, Boll (CH); Kate Gerber, Bern (CH); Kerstin Thorwarth, Lindau (CH); Aarati Chacko, Bogis-Bossey (CH); Jorg Patscheider, Meilen (CH)

( * ) Notice: Subject to any disclaimer, the term of this patent is extended or adjusted under 35 U.S.C. 154(b) by 928 days.

(21) Appl. No.: 16/627,725

(22) PCT Filed: Jun. 29, 2018

(86) PCT No.: PCT/EP2018/067648

§ 371 (c)(1),
(2) Date: Dec. 30, 2019

(87) PCT Pub. No.: WO2019/002578

PCT Pub. Date: Jan. 3, 2019

(65) Prior Publication Data

US 2021/0153949 A1    May 27, 2021

(30) Foreign Application Priority Data

Jun. 30, 2017   (EP) ..................................... 17179063

(51) Int. Cl.
*A61B 34/20*    (2016.01)
*A61B 17/16*    (2006.01)
(Continued)

(52) U.S. Cl.
CPC .......... *A61B 34/20* (2016.02); *A61B 17/1615* (2013.01); *A61N 1/0551* (2013.01);
(Continued)

(58) Field of Classification Search
CPC .... A61B 17/1615; A61B 34/20; A61N 1/0551
See application file for complete search history.

(56) References Cited

U.S. PATENT DOCUMENTS

2009/0306754 A1* 12/2009 Parker .................. A61N 1/0541
607/137

FOREIGN PATENT DOCUMENTS

DE    102011112087 A1 * 3/2013 ............... A61N 1/05

* cited by examiner

*Primary Examiner* — Sameh R Boles
(74) *Attorney, Agent, or Firm* — Julian D. Forman

(57) ABSTRACT

The present invention relates to an intervention device (20) for surgically intervening a target tissue of a human or animal body, comprising a penetrating body (100) arranged to be advanced into the target tissue along an advancing axis (Z+). The penetrating body (100) has an outer surface with a plurality of electrodes (e1, e2, e3, e4, . . . , eN) insulated from each other. More particularly, the penetrating body comprises a substrate base (5), a number N>1 of electrically conducting coatings ($cc_{e1}$, $cc_{e2}$, $cc_{e3}$, $cc_{e4}$, . . . , $cc_{eN}$) and a number M=N−1 electrically insulating coatings ($ic_{i1}$, $ic_{i2}$, $ic_{i3}$, . . . , $ic_{iM}$). A $1^{st}$ electrically conducting coating ($cc_{e1}$) at least partially covers the substrate base (5), whereas each $m^{th}$ electrically insulating coating of the M electrically insulating coatings $ic_{i1}$, $ic_{i2}$, $ic_{i3}$, $ic_{i4}$, . . . , $ic_{iM}$) partially covers the $m^{th}$ electrically conducting coating of the N electrically conducting coatings ($cc_{e1}$, $cc_{e2}$, $cc_{e3}$, $cc_{e4}$, . . . ) and each $n^{th}$ electrically conducting coating of the N electrically conducting coatings ($cc_{e2}$, $cc_{e3}$, $cc_{e4}$) partially covers the $(n-1)^{th}$ electrically insulating coating ($ic_{i1}$, $ic_{i2}$, $ic_{i3}$). Thus, the outer surface of the penetrating body (100) comprises at least L=N+M sections (e1, i1, e2, i2, e3, i3, e4) alternatingly formed by the N electrically conducting coatings ($cc_{e1}$, $cc_{e2}$, $cc_{e3}$, $cc_{e4}$, . . . , $cc_{eN}$) and the M electrically insulating coatings ($ic_{i1}$, $ic_{i2}$, $ic_{i3}$, . . . , $ic_{iM}$). The present (Continued)

invention also relates to a an intervention system comprising a power supply unit and an intervention device ($\mathbf{20}$; $\mathbf{200}$) as above described, wherein at least one ($cc_{e1}$) of the N electrically conducting coatings ($cc_{e1}$, $cc_{e2}$, $cc_{e3}$, $cc_{e4}$, ..., $cc_{eN}$) of the intervention device ($\mathbf{20}$; $\mathbf{200}$) is connected to the power supply unit such that it forms a cathode and at least another one ($cc_{e2}$, $cc_{e3}$, $cc_{e4}$) of the N electrically conducting coatings is an anode.

16 Claims, 5 Drawing Sheets

(51) Int. Cl.
     *A61N 1/05*      (2006.01)
     *A61B 17/00*      (2006.01)

(52) U.S. Cl.
     CPC .............. *A61B 2017/00039* (2013.01); *A61B 2034/2053* (2016.02)

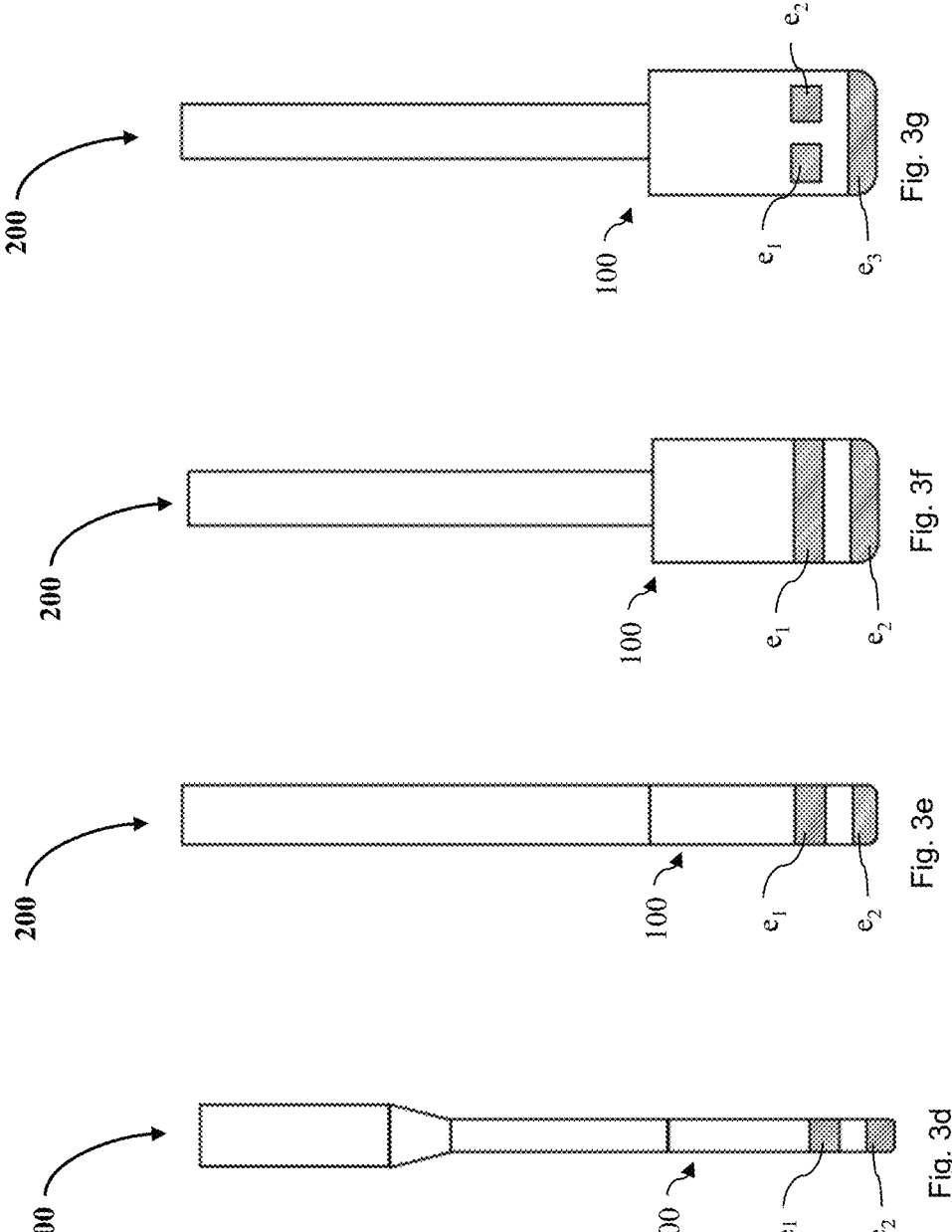

INTERVENTION DEVICE WITH ELECTRODES

CROSS-REFERENCE TO RELATED APPLICATIONS

This is a U.S. National Stage of International Application PCT/EP2018/067648, filed Jun. 29, 2018, which claims priority to European Patent Application 17179063.7, filed Jun. 30, 2017.

TECHNICAL FIELD

The present invention relates to an intervention device for surgically intervening a target tissue of a human or animal body according to the preamble of independent claim 1 and more particularly to an intervention device comprising a penetrating body whose outer surface is provided with a plurality of electrodes insulated from each other according to a specially engineered multi-layered configuration of electrically conducting coatings and electrically insulating coatings.

Such intervention devices can be used for safely, controllably and continuously intervening a target tissue, such as bone tissue or a soft tissue.

A possible application of the present invention can be, for instance, to prepare the placement of a cochlear implant, that is an electronic medical device that replaces the function of a damaged inner ear. Typically a cochlear implant comprises an internal receiver, or stimulator, which receives external signals from a speech processor and converts them into electric impulses; and an electrode array to be embedded in the cochlea, or inner ear, to directly stimulate the cochlear nerve by such electric impulses. The present invention allows to safely and efficiently prepare a bed for an internal receiver of a cochlear implant to secure it to a skull of a patient; as well as drilling small access holes in the lateral skull base for implants wire-like electrode array to be inserted into the inner ear.

Otherwise, the present invention is suitable to any use wherein an intervention on a target tissue of a human or animal body is required by way of an intervention device, such as a drill tool or a burr tool or similar, which penetrates a target tissue, while care is required that no nerve is thereby damaged or unduly interfered with.

BACKGROUND ART

Implantation of any prosthetic element (whether dental, craniomaxillofacial, articular, spinal etc.) in a body requires that maximum attention is paid to preventing injury of adjacent nerves and that the drilling of a hole for the prosthetic part take into account the overall anatomical configuration of an intervened body part or tissue.

It is established practice to use intraoperative monitoring to localize neural structures, for example to locate cranial nerves during skull base surgery; to test function or response of these structures; and to preserve integrity of such neural structures during surgery, for instance by allowing for prompt corrective measures.

To this purpose, normally electrophysiological signals from the patient are triggered, for instance by activation of stimulating electrodes at given times. Responses are detected, for instance by recording electrodes, through the course of an operation. Thanks to a connected computer system and a dedicated software running on it, the electrophysiological signals coming from the patient and picked up by the recording electrodes can be processed and interpreted, namely for construing a distance to a neural structure. Several methods can be used to stimulate nerves and process relative response signals. For instance, electromyography allows to draw conclusions on the distance to a nerve during intervention based on the extent of the activity of a muscle associated with such nerve. Nerve stimulation produces a muscle response which, in turn, is representative of nerve detection. By processing the response signals, an assessment of a distance between a nerve and a device, such as a probe, emitting the stimulation signals can be carried out. Typically, a prediction distance from a neural structure can be estimated, with a statistical probability that such prediction distance equals each one of a range of predefined distance values from the neural structure, according to a statistical distribution. Thus, the likelihood that a device is positioned at a certain distance from a neural structure (for instance, out of a discrete number of possible distance values) can be taken into account during a surgical intervention procedure for early prevention of intraoperative neural injury.

To date, nerve stimulation systems for the purpose of intraoperative neurophysiological monitoring mainly comprise stationary stimulation probes integrating a plurality of stimulation electrodes, which can be separated by non-conductive material, for instance being embedded in a resin holding structure.

In the scientific article by Juan Ansö et al., titled "A neuromonitoring approach to facial nerve preservation during image-guided robotic cochlear implantation", published in "Otology & Neurology" in 2015, a multipolar facial nerve stimulation probe is disclosed, wherein four independent electrodes are embedded into an elongated support structure made of resin. In FIG. 1 of this article, a tip electrode functions as a cathode, whereas three ring-like electrodes function as anodes, for bipolar nerve stimulation.

A surgical intervention with the aid of a neuromonitoring probe such as in the above article necessarily entails interruptions of the surgical intervention. In fact, a hole-drilling operation by a separate intervention tool such as a drill bit needs to be interrupted in order to allow for the distinct probe to be inserted to carry out the nerve stimulation and monitoring. Therefore, the surgical intervention would not actually comprise continuous measuring and monitoring but would need to be split in several successive phases of either drilling or neuromonitoring.

Moreover, the discrete ring-like electrodes used in the disclosed neuromonitoring probe are not easily sizable along the elongated support structure and, as a consequence, are not suitable to create an array of spatially distinct surface electrodes, differently scaled to enable a wide variety of multiple electrical field distributions on the substrate body, or support structure, of a surgical tool. Accordingly, in the case portrayed in FIG. 1 of the mentioned article, the sensitivity to the presence of a neural structure cannot be extra-finely modulated by a wide variety of multiple electrical field distributions on the substrate body.

Additionally, the discrete ring-like electrodes used in the neuromonitoring probe of the article are not best configured to redirect the signals corresponding to the detected stimulus response from the probe to a processing unit.

There are commercially available surgical tools, suitable to create holes in a tissue such as bone, which integrate nerve stimulation means and/or nerve response sensing means and/or tissue characterization means. However, they are not structured in a way that the incorporated electrodes effectively enable multiple electrical field distributions for a multipolar characterization of electrical properties at an electrode-tissue (or electrode-cell) interface.

Namely, U.S. Pat. No. 8,326,414 B2 discloses a nerve stimulating drill bit, comprising a conductor extending through a shank and a body of the drill bit and an insulation sleeve. The conductor can provide a nerve stimulating signal at the cutting tip of the drill bit. Configurations with either one or two stimulating electrodes at the tool tip are given. In U.S. Pat. No. 8,326,414 B2, it is purposely intended to focus the stimulation on the tissue proximate to the cutting tip of the nerve stimulating drill bit.

One of the main drawbacks of the stimulating drill bit of U.S. Pat. No. 8,326,414 B2 lies in that the electric field created at the point of the drill bit remains very narrow and localized, therefore not being very versatile or adaptable to a multiplicity of nerve detection situations. There also exists a risk of short circuit, as a consequence of such structure.

Therefore, there is a need for an intervention device or process for surgically intervening a target tissue of a human or animal body such that:

execution of the surgical intervention is guaranteed to be carried out in a controlled way, taking into account a given anatomical and neurophysiological situation;
the surgical intervention and the probing for neuromonitoring are efficiently performed;
while ensuring precision in neuromonitoring and transferring the detected response from a neural structure, the intervention device is robust enough to perform the intended penetration and advancement into a target tissue of a body of a patient; and/or
the surgical intervention can be carried out adaptively, based on an optimal and reliable collection of data from the concurrent neuromonitoring and on an ensuing estimation of a prediction distance from a neural structure.

DISCLOSURE OF THE INVENTION

According to the invention this need is settled by an intervention device as it is defined by the features of independent claim 1, and by an intervention system as it is defined by the features of independent claim 12. Preferred embodiments are subject of the dependent claims.

In particular, the invention deals with an intervention device for surgically intervening a target tissue of a human or animal body, comprising a penetrating body arranged to be advanced into the target tissue preferably along an advancing axis. The term "intervention" as use herein particularly relates to an act of surgery or operating a patient. The intervention can be involved in a surgical procedure, operation or surgery.

More specifically, in an intervention as understood herein, a tissue or organ of the patient is changed or adapted by cutting, drilling, milling or a similar operation. For that purpose, the intervention device has the penetrating body which is embodied to be advanced into the target tissue. Thus, different from placing an element in an existing cavity such as a body cavity, by means of the penetrating body the intervention device creates its own path into the target tissue.

The penetrating body has an outer surface with a plurality of electrodes insulated from each other. More specifically, the penetrating body comprises a substrate base, a number $N>1$ of electrically conducting coatings and a number $M=N-1$ electrically insulating coatings.

The structure of the penetrating body is configured such that a $1^{st}$ electrically conducting coating at least partially covers the substrate base, each $m^{th}$ electrically insulating coating of the M electrically insulating coatings partially covers the $m^{th}$ electrically conducting coating of the N electrically conducting coatings and each $n^{th}$ electrically conducting coating of the N electrically conducting coatings partially covers the $(n-1)^{th}$ electrically insulating coating.

Consequently, the outer surface of the penetrating body comprises at least $L=N+M$ sections alternatingly formed by the N electrically conducting coatings and the M electrically insulating coatings.

In the context of the present invention, N and M are fixed numbers and n and m are associated variables. For instance, when we there are four electrically conducting coatings and three electrically insulating coatings, N is 4 and M is 3, whereas n is 1, 2, 3 or 4 and m is 1, 2 or 3. Thus, $n \in \{1, \ldots, N\}$ and $m \in \{1, \ldots, M\}$, wherein $M=N-1$.

Preferably, the partial covering of the $(n-1)^{th}$ electrically insulating coating by the $n^{th}$ electrically conducting coating of the N electrically conducting coatings starts with $n=2$, i.e. the sequence starts with the second electrically conducting coating partially covering the first electrically insulating coating. As a result, the outer surface of the penetrating body of intervention device comprises a staggered series of alternating portions electrically conducting coatings and electrically insulating coatings which continually overlap.

Preferably, the penetrating body comprises a base electrically insulating coating located between the substrate base and the $1^{st}$ electrically conducting coating. This is especially advantageous if the substrate base is electrically conducting.

The penetrating body may also comprise a final electrically insulating coating partially covering the $n^{th}=N$ electrically conducting coating.

Preferably, the intervention device according to the present invention can take the form of a surgical drill bit, a cutting bur, a milling bur or another material removing tool, at the same time advantageously integrating the stimulating and sensing functions of a probe.

At any rate, an intervention device according to the present invention can be any surgical tool designed for removing tissue material, suitable for operations such as milling, drilling, burring, cutting, shaving, grasping. Alternatively, the intervention device according to the present invention may also be a tool suited for performing operations not entailing material removal, for instance taking the form of needles, trocars or energy applicators, wherein the penetrating body of the device may dynamically move (e.g. by way of rotation; oscillation; translation or a combination thereof) or even remain stationary or static.

A multi-layered structure of the intervention device as above illustrated, wherein an array of surface electrodes is provided by electrically conducting coatings alternated with partially overlapping electrically insulating coatings, advantageously enables the creation of multiple electrical field distributions around the substrate base.

Each of the electrical field distributions enables several configurations for multipolar characterization of electrical properties at the electrode-tissue (or cell culture) interface.

Thanks to the special structural arrangement of the intervention device according to the present invention, wherein a multiplicity of electrodes are provided at a number of different distances along the outer surface of the penetrating body, several electrical field distributions can be created according to respective electrode configurations. Hence, the neuromonitoring sensitivity is improved and the measurements are carried out with an increased spatial resolution. Not only that, but given the substantial continuity of the electrical conductive coatings up to at least one proximal end of the substrate base (i.e. the extremity that is least advanced in the penetration of the target tissue and that is opposed to a distal tip of the intervention device), the transfer of the detected response from a neural structure to a connected computer-based processing unit is operatively simplified and can be made seamlessly without the need for complicated interfaces.

Additionally, return electrodes at short distances from the tool tip provide for different variations of the electrical field distribution functions surrounding the tip.

Further, electrodes may be produced on the outer surface of the tool by means of masked deposition or by some other additive method. Therefore, different electrode sizes and shapes can simply be manufactured by modifications of the masking concept or of some other deposition concept. For instance, a smaller effective-surface area of an active stimulating electrode may be desired to provide higher current density at specific location of the tool. Moreover, an extensive variation of electrode shapes can be created on the substrate base, such as spherical, conical, or other types. The deposition of the electrically conducting coatings and of the electrically insulating coatings can be carried out by known techniques for the creation of thin films, such as physical vapor deposition e.g. by sputtering or by plasma-spray evaporation.

A multi-layered structure produced as above described, with a substrate base core and, on top of this, a stratification of partially overlapping coatings, is inherently robust and optimally bears mechanical stresses which can be applied during a surgical intervention, even on hard bone tissue.

Such robustness makes the intervention device according to the present invention suitable for an integrated use both as a measuring device, carrying out for instance the function of a probe, and as a generic rotating or dynamic tool for making holes or perforating a tissue, such as in the case of a drill bit or of a bur. Thus, a surgical intervention and the probing for neuromonitoring are enabled concurrently and can happen continuously thanks to the use of one same intervention device according to the present invention.

Preferably, the substrate base is made of a medical grade material compatible with the physical requirements of an intended operation of the intervention device, e.g. a machining operation, such as a medical steel material. The medical steel material can be, e.g., tungsten carbide (WC) or stainless steel. The substrate base can also be made of diamond.

Preferably, the M electrically insulating coatings are made of a medical grade material compatible with the physical requirements of an intended operation of the intervention device, e.g. a machining operation, such as silicon nitride ($Si_3N_4$), whereas the N electrically conducting coatings are preferably made of a medical grade material compatible with the physical requirements of an intended operation of the intervention device, e.g. a machining operation, such as titanium nitride (TiN).

Preferably, the M electrically insulating coatings and the N electrically conducting coatings are arranged such that the at least L=N+M sections of the outer surface of the penetrating body are rings extending about the advancing axis.

In a possible embodiment, the M electrically insulating coatings and the N electrically conducting coatings are arranged such that the at least L=N+M sections of the outer surface of the penetrating body comprise strings along the advancing axis. Such strings can thus create different patterns of electrically conducting coatings, like linear oblong elements extending along the advancing axis. Depending on the shape of the substrate base, the incorporation of electrodes bearing the shape of segments of sphere or of otherwise shaped electrode portions (e.g. cylindrical, conical or a combination thereof) is also possible.

Preferably, the intervention device comprises an amplifier unit arranged to measure tissue impedance between plural electrodes formed N electrically conducting coatings ($cc_{e1}$, $cc_{e2}$, $cc_{e3}$, $cc_{e4}$, . . . , $cc_{eN}$).

Preferably, the penetrating body of the intervention device has a front end and a back end, wherein the plurality of electrodes insulated from each other is located near the front end of the penetrating body, and an identical plurality of corresponding electrodes insulated from each other is provided near the back end of the penetrating body. Thereby, each of the electrically conducting coatings preferably forms one of the electrodes near the front end of the penetrating body and one of the corresponding electrodes near the back end of the penetrating body. Like this, pairs of electrodes are formed which are connected by the respective electrically conducting coating. Such an arrangement of electrodes at the front and back ends allows for contacting the electrodes, e.g., for providing a voltage in order to generate an electromagnetic or an electric field or for other purposes.

The present invention also relates to an intervention system comprising a power supply unit and an intervention device as above described, wherein at least one of the N electrically conducting coatings of the intervention device is connected to the power supply unit such that it forms a cathode and at least another one of the N electrically conducting coatings is an anode. Such an intervention system allows for achieving the effects and benefits described in connection with the above intervention device and its preferred embodiments.

Preferably, the at least one of the N electrically conducting coatings connected to the power supply unit is the $1^{st}$ electrically conducting coating. The $1^{st}$ electrically conducting coating is preferably cone shaped and substantially forms the outer surface of the penetrating body at the tip of the intervention device.

According to the above configuration, preferably the electrically conducting coatings other than the $1^{st}$ electrically conducting coating are anodes.

An intervention system according to the present invention may also comprise a relay unit arranged to switch between plural of the at least one anode. Thus, advantageously, the power supply unit can be switched among the several cathode-anode configurations provided i.e. among the corresponding several electrical field distributions, created on and around the intervention device. Thanks to this versatility in commuting between different electrical filed distributions, it is made easier to detect potential nerve collision in different orientations and directions, e.g. differently angled frontal or lateral collisions.

Preferably, an intervention system according to the present invention comprises an amplifier unit arranged to measure low signal voltages between plural electrodes formed by the N electrically conducting coatings. For example, the plural electrodes can comprise the at least one cathode and one anode, or one cathode and two anodes, or one cathode and three anodes. Thus, different electrical field volume conductors can be created between each of cathode-anode pairs and a response from a neural structure to a stimulus can be optimally detected and recorded.

In a particular embodiment of the intervention system, the power supply unit can be arranged to provide electric sinewave or other type of periodic waves signals having a temporal period between about 1 µs and 1 s, or between about 10 µs and about 100 ms, or between about 100 µs and about 10 ms.

The above sinewave or other wave type signals may be in a range of about 1 µA to about 100 µA, or between about 10 µA and about 50 µA, or between 1 mV and about 1 V.

In a different possible embodiment of the intervention system, the power supply unit may be arranged to provide electric current pulses having a temporal width between about 50 µs and about 500 µs, or between about 100 µs and about 400 µs, or between about 150 µs and about 300 µs, or of about 250 µs.

Preferably, such current pulses are in a range of about 0.1 mA to about 1 mA or of about 0.1 mA to about 30 mA.

An intervention system according to the present invention preferably comprises a processing unit arranged to compute or calculate geometric properties of said tool with respect to a target anatomy such as a nerve and based on the electric signals perceived from the at least one anode and an electric activity of a muscle.

It can additionally or alternatively comprises a processing unit arranged to evaluate a distance to a nerve based on an electric signal sent and/or perceived at the at least one anode or at least one electrode and an electric activity of a muscle. The structure of the intervention device as introduced optimizes the capacity to correlate the stimulation of a neural structure and of an associated muscle, as well as the detected response given to such stimulation, to a prediction distance from the neural structure, for a continuously reliable, real-time assessment of the safety of an on-going intervention.

The point of the intervention device according to the present invention, or the distal end thereof—that is, the extremity which in operation is most advanced into the target tissue along the advancing axis—may also incorporate further functional elements, preferably acting as sensing elements, capable of measuring a variety of electrical, mechanical, electro-mechanical or thermal parameters. By way of example, the $1^{st}$ electrically conducting coating, acting preferably as cathode electrode, may be designed to also perform other functional tasks, such as measuring the electrical impedance of the tissue encountered during the insertion process. Thus, the intervention device can give indications on the nature of tissue intervened e.g. whether a bone portion encountered consists of cortical or cancellous bone tissue. Alternatively or additionally to that, a temperature sensor may be incorporated at the point, for instance created through a two different material thermo-coupling principle; and/or a strain gauge to measure mechanical tensile and compressive forces acting on the intervention device as it progressively advances into the target tissue; and/or an electrochemical sensor to measure electrical or electrochemical properties (e.g. the pH variation) of tissue or cell cultures. The distal end of the intervention device may further be provided with actuation elements such as radiofrequency antennas, thermal heating elements or a combination thereof.

BRIEF DESCRIPTION OF THE DRAWINGS

The intervention device according to the invention is described in more detail herein below by way of exemplary embodiments and with reference to the attached drawings, in which:

FIG. 1 shows a schematic representation of a first embodiment of an intervention device according to the present invention, in the form of a drill bit, by way of:

Figure 2B:
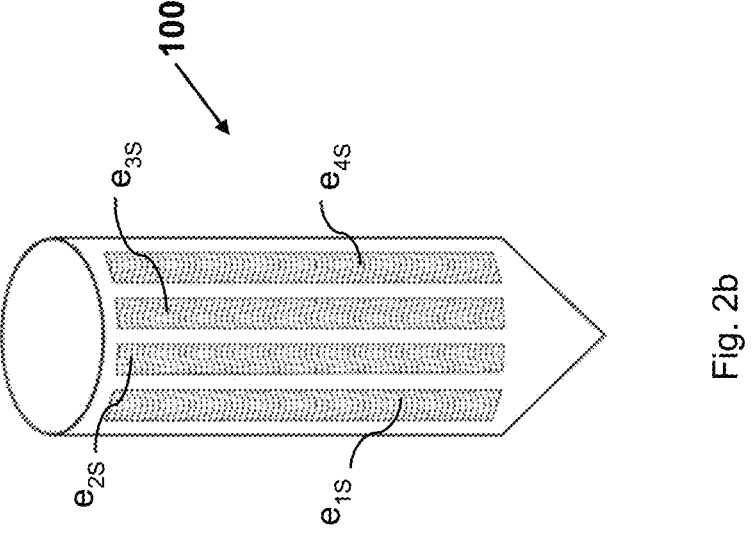
Figure 2A:
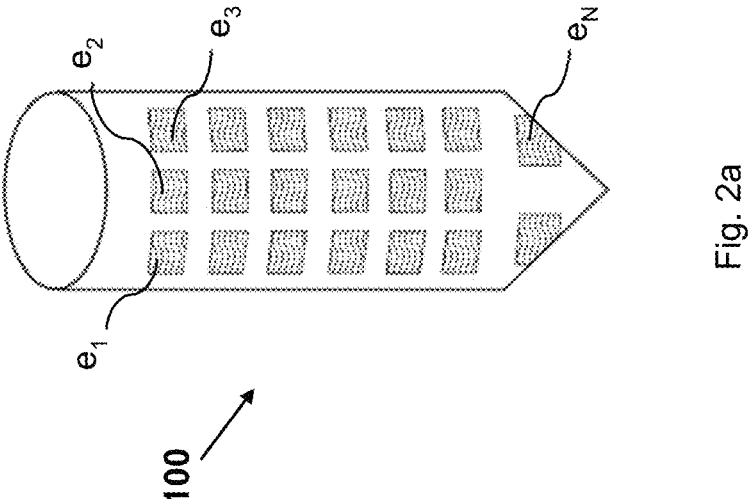
Figures 3A, 3B, 3C:
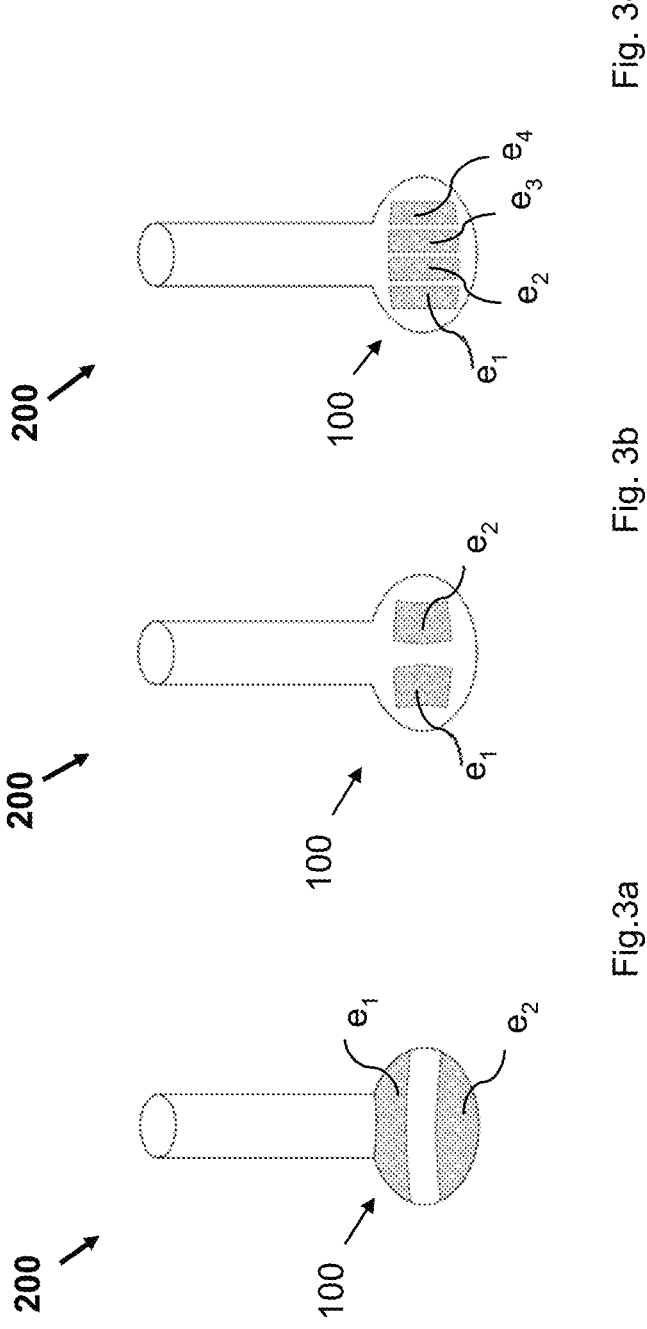

a side view in a plane (Y−, Z+), highlighting how M electrically insulating coatings and N electrically conducting coatings are arranged so that respective rings are produced which alternatingly extend about an advancing axis; and a cross-sectional view in a plane (Y+, Z+) highlighting how an $n^{th}$ electrically conducting coating of the N electrically conducting coatings partially covers an $(n-1)^{th}$ electrically insulating coating of the M electrically insulating coatings;

FIGS. 2a and 2b show a second and a third possible embodiment of intervention devices according to the present invention, in the form of respective drill bits, having sections of the outer surface of the penetrating bodies comprising differently shaped and distributed strings along the advancing axis; and FIGS. 3a, 3b, 3c, 3d, 3e, 3f and 3g respectively show further embodiments of intervention devices according to the present invention, in the form of burrs having respective different arrangements of electrically conducting coatings and of electrically insulating coatings.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1A:
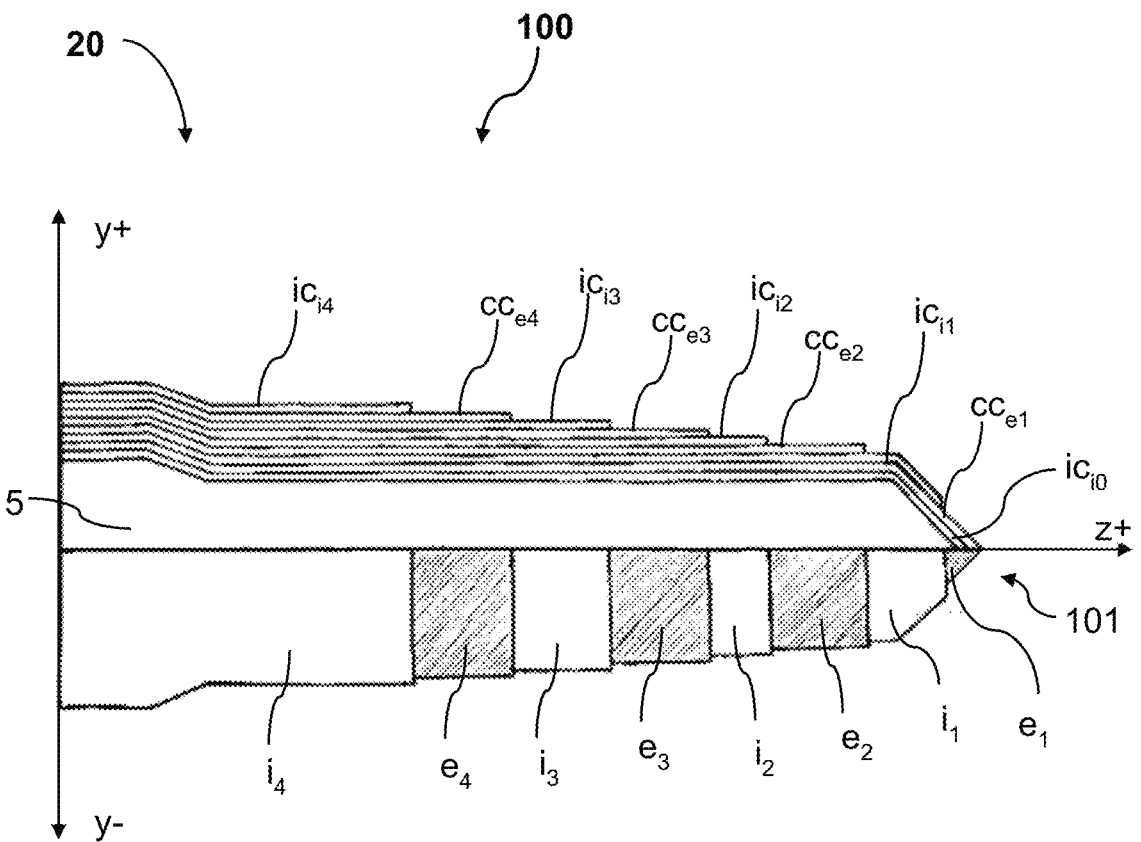
Figure 1B:
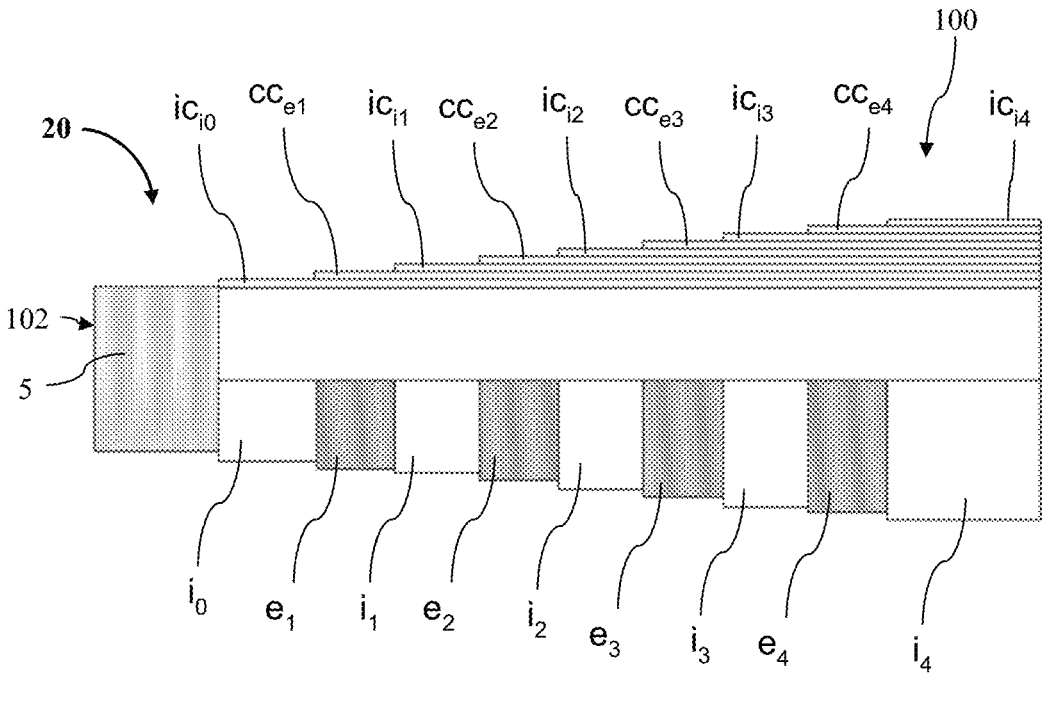

Referring to the embodiment of FIG. 1a and FIG. 1b, an intervention device for surgically intervening a target tissue of a human or animal body according to the present invention takes the form of a surgical drill bit 20 and comprises a penetrating body 100 with a sharp front end 101 or distal end arranged to be advanced into the target tissue along an advancing axis Z+ and a flat back end 102 or proximal end.

At each of the front and back ends 101, 102, the penetrating body 100 has an outer surface with four electrodes $e_1$, $e_2$, $e_3$, $e_4$ which are insulated from each other by three insulating sections $i_1$, $i_2$ and $i_3$. It further comprises a substrate base 5, acting as support.

The electrodes $e_1$, $e_2$, $e_3$, $e_4$ and the insulating sections $i_1$, $i_2$, $i_3$ there between are actually created by a special arrangement of four electrically conducting coatings $cc_{e1}$, $cc_{e2}$, $cc_{e3}$, $cc_{e4}$ and three electrically insulating coatings $ic_{i1}$, $ic_{i2}$, $ic_{i3}$.

The $1^{st}$ electrically conducting coating $cc_{e1}$ covers the substrate base 5. Moreover, each insulating coating $ic_{i1}$, $ic_{i2}$, $ic_{i3}$, partially covers a respective electrically conducting coating $cc_{e1}$, $cc_{e2}$, $cc_{e3}$; whereas each electrically conducting coating $cc_{e2}$, $cc_{e3}$, $cc_{e4}$ partially covers a respective underlying electrically insulating coating $ic_{i1}$, $ic_{i2}$, $ic_{i3}$.

The special arrangement above is such that the outer surface of the penetrating body 100 comprises sections $e_1$, $i_1$, $e_2$, $i_2$, $e_3$, $i_3$, $e_4$ alternatingly formed by the four electrically conducting coatings $cc_{e1}$, $cc_{e2}$, $cc_{e3}$, $cc_{e4}$ and the three electrically insulating coatings $ic_{i1}$, $ic_{i2}$, $ic_{i3}$. Accordingly, these sections take the form of rings $e_1$, $i_1$, $e_2$, $i_2$, $e_3$, $i_3$, $e_4$ extending about the advancing axis Z+. The first electrically conducting coating $cc_{e1}$, forms, in cooperation with electrically insulating coatings $ic_{i1}$, section e1 which, at the front end 101, is a substantially cone-shaped electrode and functions as the tip of the drill bit 20. Electrically conducting coating $cc_{e1}$, is connected to a power supply unit at section $e_1$ at the back end 102 and forms a cathode at section e1 at the front end 101. Sections $e_2$, $e_3$ and $e_4$, created by corresponding partially overlapped electrically conducting coatings $cc_{e2}$, $cc_{e3}$, $cc_{e4}$, are electrodes functioning as anodes. Thereby, since the sections $e_2$ to $e_4$ are also accessible at the back end 102, they can be contacted. Since in use the drill bit 20 is rotating, contacting of the electrodes can, e.g., be implemented by means of brushes or the like.

In the specific embodiment represented in FIG. 1, the penetrating body 100 comprises a base electrically insulating coating $ic_{i0}$, located between the substrate base 5 and the $1^{st}$ electrically conducting coating $cc_{e1}$. This additional design feature is especially useful when the substrate base 5 itself is electrically conducting.

In addition to that, the penetrating body 100 comprises a final electrically insulating coating $ic_{i4}$, which is partially covering the fourth electrically conducting coating $cc_{e4}$ and forms a further insulating section $i_4$ on the outer surface of the penetrating body 100.

The substrate base 5 is in this case made of a medical steel material, such as tungsten carbide (WC) or stainless steel. Otherwise, the substrate base can also be made of diamond or any other suitable material.

The three electrically insulating coatings $ic_{i1}$, $ic_{i2}$, $ic_{i3}$ are made of silicon nitride. Analogously, also the final electrically insulating coating $ic_{i4}$ is made of silicon nitride.

The four electrically conducting coatings $cc_{e1}$, $cc_{e2}$, $cc_{e3}$, $cc_{e4}$ are made of titanium nitride.

Referring to the embodiments of FIGS. 2a and 2b, the electrically insulating coatings and the electrically conducting coatings are arranged such that strings, or strips, of conducting material of variable elongation are created. In FIG. 2a, the outer surface sections $e_1$, $e_2$, $e_3$, . . . , $e_N$ create a checkered or spotted pattern of electrodes. In FIG. 2b, the outer surface sections $e_{1s}$, $e_{2s}$, $e_{3s}$, $e_{4s}$ are oblong strips of conducting material forming substantially parallel electrodes which extend along an advancing axis corresponding to the advancement in the target tissue of the penetrating body 100 of the intervention device.

Based on the shape of the substrate base of the intervention device 200 supporting the multi-layered structure, the electrically insulating and electrically conducting coatings can be arranged to create sections of the outer surface of the penetrating body 100 which incorporate electrodes $e_1$, $e_2$, $e_3$, $e_4$ of different form, as shown in FIGS. 3a, 3b, 3c, 3d, 3e, 3f and 3g for three burr-like intervention devices. In particular, the sections forming the electrodes can be segments of sphere or spherical strips of different type.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. Intervention device (20; 200) consisting of a surgical drill bit for surgically intervening a target tissue of a human or animal body, comprising a penetrating body (100) arranged to be advanced into the target tissue preferably along an advancing axis (Z+), wherein the penetrating body (100) has an outer surface with a plurality of electrodes ($e_1$, $e_2$, $e_3$, $e_4$, . . . , $e_N$) insulated from each other, characterized in that the penetrating body (100) comprises a substrate base (5), a number N>1 of electrically conducting coatings ($cc_{e1}$, $cc_{e2}$, $cc_{e3}$, $cc_{e4}$, . . . , $cc_{eN}$) and a number M=N−1 electrically insulating coatings ($ic_{i1}$, $ic_{i2}$, $ic_{i3}$, $ic_{i4}$, . . . , $ic_{iM}$), wherein a $1^{st}$ electrically conducting coating ($cc_{e1}$) at least partially covers the substrate base (5), each $m^{th}$ electrically insulating coating of the M electrically insulating coatings ($ic_{i1}$, $ic_{i2}$, $ic_{i3}$, . . . , $ic_{iM}$) partially covers the $m^{th}$ electrically conducting coating of the N electrically conducting coatings ($cc_{e1}$, $cc_{e2}$, $cc_{e3}$, $cc_{e4}$, . . . ) and each $n^{th}$ electrically conducting coating of the N electrically conducting coatings ($cc_{e2}$, $cc_{e3}$, $cc_{e4}$) partially covers the $(n−1)^{th}$ electrically insulating coating ($ic_{i1}$, $ic_{i2}$, $ic_{i3}$) such that the outer surface of the penetrating body (100) comprises at least L=N+M sections ($e_1$, $i_1$, $e_2$, $i_2$, $e_3$, $i_3$, $e_4$) alternatingly formed by the N electrically conducting coatings ($cc_{e1}$, $cc_{e2}$, $cc_{e3}$, $cc_{e4}$, . . . , $cc_{eN}$) and the M electrically insulating coatings ($ic_{i1}$, $ic_{i2}$, $ic_{i3}$, . . . , $ic_{iM}$).

2. Intervention device (20; 200) according to claim 1, wherein the penetrating body (100) comprises a base electrically insulating coating ($ic_{i0}$) located between the substrate base (5) and the $1^{st}$ electrically conducting coating ($cc_{e1}$).

3. Intervention device (20; 200) according to claim 1, wherein the penetrating body (100) comprises a final electrically insulating coating ($ic_{i4}$).

4. Intervention device (20; 200) according to claim 1, wherein the substrate base (5) is made of a medical grade material compatible with the physical requirements of an intended operation of the intervention device (20; 200), e.g. a machining operation, such as a medical steel material.

5. Intervention device (20; 200) according to claim 1, wherein the M electrically insulating coatings ($ic_{i1}$, $ic_{i2}$, $ic_{i3}$, . . . , $ic_{iM}$) are made of a medical grade material compatible with the physical requirements of an intended operation of the intervention device (20; 200), e.g. a machining operation, such as silicon nitride.

6. Intervention device (20; 200) according to claim 1, wherein the N electrically conducting coatings ($cc_{e1}$, $cc_{e2}$, $cc_{e3}$, $cc_{e4}$, . . . , $cc_{eN}$) are made of a medical grade material compatible with the physical requirements of an intended operation of the intervention device (20; 200), e.g. a machining operation, such as titanium nitride.

7. Intervention device (20; 200) according to claim 1, wherein the M electrically insulating coatings ($ic_{i1}$, $ic_{i2}$, $ic_{i3}$, . . . , $ic_{iM}$) and the N electrically conducting coatings ($cc_{e1}$, $cc_{e2}$, $cc_{e3}$, $cc_{e4}$, . . . , $cc_{eN}$) are arranged such that the at least L=N+M sections of the outer surface of the penetrating body are rings ($e_1$, $i_1$, $e_2$, $i_2$, $e_3$, $i_3$, $e_4$) extending about the advancing axis (Z+).

8. Intervention device (20; 200) according to claim 1, wherein the M electrically insulating coatings ($ic_{i1}$, $ic_{i2}$, $ic_{i3}$, . . . , $ic_{iM}$) and the N electrically conducting coatings ($cc_{e1}$, $cc_{e2}$, $cc_{e3}$, $cc_{e4}$, . . . , $cc_{eN}$) are arranged such that the at least L=N+M sections of the outer surface of the penetrating body comprise strings ($e1_s$, $e2_s$, $e3_s$, $e4_s$) along the advancing axis (Z+).

9. Intervention device according to claim 1, wherein the penetrating body (100) has a front end (101) and a back end (102), the plurality of electrodes ($e_1$, $e_2$, $e_3$, $e_4$, . . . , $e_N$) insulated from each other is located near the front end (101) of the penetrating body (100), and an identical plurality of corresponding electrodes ($e_1$, $e_2$, $e_3$, $e_4$, . . . , $e_N$) insulated from each other is provided near the back end (102) of the penetrating body (100).

10. Intervention device according to claim 9, wherein each of the electrically conducting coatings ($cc_{e1}$, $cc_{e2}$, $cc_{e3}$, $cc_{e4}$, . . . , $cc_{eN}$) forms one of the electrodes ($e_1$, $e_2$, $e_3$, $e_4$, . . . , $e_N$) near the front end (101) of the penetrating body (100) and one of the corresponding electrodes ($e_1$, $e_2$, $e_3$, $e_4$, . . . , $e_N$) near the back end (102) of the penetrating body (100).

11. Intervention device (20; 200) according to claim 1, further comprising a power supply unit wherein at least one ($cc_{e1}$) of the N electrically conducting coatings ($cc_{e1}$, $cc_{e2}$, $cc_{e3}$, $cc_{e4}$, . . . , $cc_{eN}$) of the intervention device (20; 200) is connected to the power supply unit such that it forms a cathode and at least another one ($cc_{e2}$, $cc_{e3}$, $cc_{e4}$) of the N electrically conducting coatings is an anode.

12. Intervention device according to claim 11, wherein the at least one of the N electrically conducting coatings ($cc_{e1}$, $cc_{e2}$, $cc_{e3}$, $cc_{e4}$, . . . , $cc_{eN}$) IS the $1^{st}$ electrically conducting coating ($cc_{e1}$).

13. Intervention device according to claim 12, wherein the electrically conducting coatings ($cc_{e2}$, $cc_{e3}$, $cc_{e4}$, . . . , $cc_{eN}$) other than the $1^{st}$ electrically conducting coating ($cc_{e1}$) are anodes.

14. Intervention device according to claim 13, comprising a relay unit arranged to switch between plural ($cc_{e2}$, $cc_{e3}$, $cc_{e4}$) of the at least one anode.

15. Intervention device system according to claim 14, comprising a processing unit arranged to compute or calculate geometric properties of said tool with respect to a target anatomy such as a nerve and based on the electric signals perceived from the at least one anode and an electric activity of a muscle.

16. Intervention device according to claim 15, comprising an amplifier unit arranged to measure low signal voltages between plural electrodes formed N electrically conducting coatings ($cc_{e1}$, $cc_{e2}$, $cc_{e3}$, $cc_{e4}$, . . . , $cc_{eN}$).

\* \* \* \* \*